(12) United States Patent
Mäkel et al.

(10) Patent No.: US 10,029,119 B2
(45) Date of Patent: *Jul. 24, 2018

(54) BRACHYTHERAPY APPLICATOR DEVICE FOR INSERTION IN A BODY CAVITY

(71) Applicant: Nucletron Operations B.V., Veenendaal (NL)

(72) Inventors: René Gerard Willem Mäkel, Arnhem (NL); Pieter Morssink, Bel Air, MD (US); Hendrik Steller, Rhenen (NL); Arie Luite Visscher, Driebergen (NL); Cor van de Wardt, Kesteren (NL); Franciscus Antonius Maria Kuipers, Veenendaal (NL)

(73) Assignee: NUCLETRON OPERATIONS B.V., Veenendaal (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/818,936

(22) Filed: Aug. 5, 2015

(65) Prior Publication Data

US 2015/0335913 A1   Nov. 26, 2015

Related U.S. Application Data

(62) Division of application No. 13/807,552, filed as application No. PCT/NL2011/050474 on Jun. 30, 2011, now Pat. No. 9,132,282.
(Continued)

(30) Foreign Application Priority Data

Jun. 30, 2010   (NL) ..................... 2005005

(51) Int. Cl.
  *A61N 5/10*   (2006.01)

(52) U.S. Cl.
  CPC ......... *A61N 5/1014* (2013.01); *A61N 5/1016* (2013.01); *A61N 2005/1094* (2013.01)

(58) Field of Classification Search
  CPC .......... A61N 5/1016; A61N 2005/1004; A61N 2005/1012; A61N 2005/1094; A61N 5/1014
  See application file for complete search history.

(56) References Cited

U.S. PATENT DOCUMENTS 4,004,299 A * 1/1977 Runge ................. A61M 1/1046
                                                              623/3.18
4,350,151 A    9/1982 Scott
(Continued)

FOREIGN PATENT DOCUMENTS

CN    101056670 A    10/2007
DE    44 13 490 C1    8/1995
(Continued)

OTHER PUBLICATIONS

International Search Report from the European Patent Office in PCT/EP2011/050474 dated Oct. 6, 2011 (2 pages).
(Continued)

*Primary Examiner* — Christine H Matthews
(74) *Attorney, Agent, or Firm* — Finnegan, Henderson, Farabow, Garrett & Dunner LLP

(57) ABSTRACT

The invention relates to a brachytherapy applicator device for insertion in a body cavity. The applicator device comprises an applicator shaped for insertion in the body cavity; the applicator comprising connectable segments; at least one connectable part having a form following wall surface shaped to follow the body cavity, the wall surface having a multichannel groove structure, so as to guide a plurality of catheters along the grooves in the groove structure along the wall surface.

19 Claims, 13 Drawing Sheets

Related U.S. Application Data

(60) Provisional application No. 61/365,004, filed on Jul. 16, 2010.

(56) References Cited

U.S. PATENT DOCUMENTS

| | | | |
|---|---|---|---|
| 9,132,282 B2* | 9/2015 | Makel et al. | A61N 5/1016 |
| 2002/0077550 A1* | 6/2002 | Rabiner | A61B 17/22012 |
| | | | 600/439 |
| 2007/0282154 A1 | 12/2007 | Puthawala | |
| 2009/0234178 A1 | 9/2009 | Lebovic et al. | |
| 2010/0298851 A1* | 11/2010 | Nield | A61B 17/320068 |
| | | | 606/169 |
| 2011/0224478 A1 | 9/2011 | Harmoun-Levi et al. | |

FOREIGN PATENT DOCUMENTS

| | | |
|---|---|---|
| EP | 1 374 951 A1 | 1/2004 |
| RU | 2325139 C1 | 5/2008 |
| RU | 2379021 C1 | 1/2010 |
| WO | WO 2006/027253 A1 | 3/2006 |
| WO | WO 2010/036103 A2 | 4/2010 |

OTHER PUBLICATIONS

Notification of Transmittal of the International Preliminary Report on Patentability and International Preliminary Report on Patentability from the European Patent Office in PCT/EP2011/050474 dated Nov. 6, 2012 (6 pages).

Official Action, issued in corresponding Russian Application No. 2013103770/14(005446), dated Feb. 5, 2015 (8 pages including English language translation).

Official Decision on Grant, issued in the corresponding Russian Application No. 2013103770/14(005446), dated Mar. 27, 2015, 4 pp.

* cited by examiner

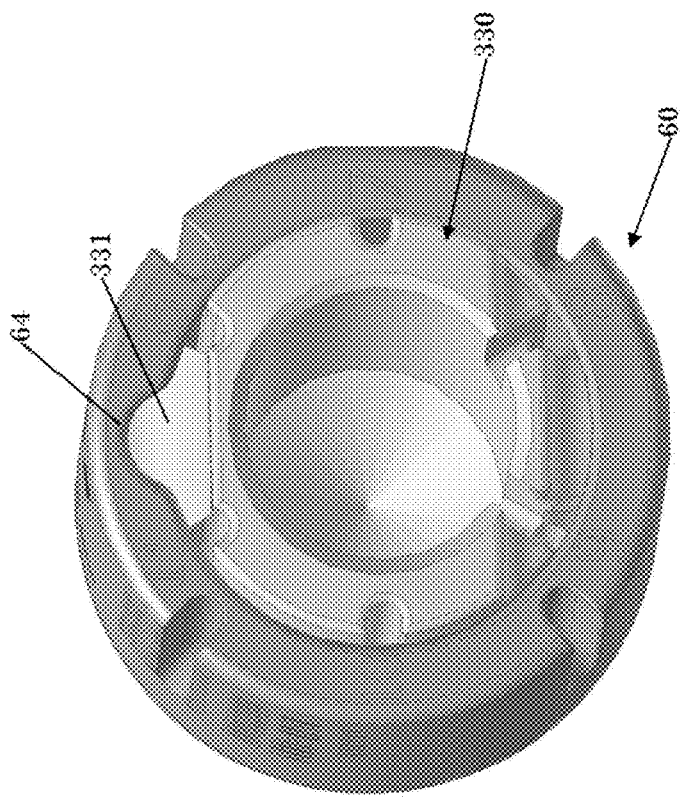
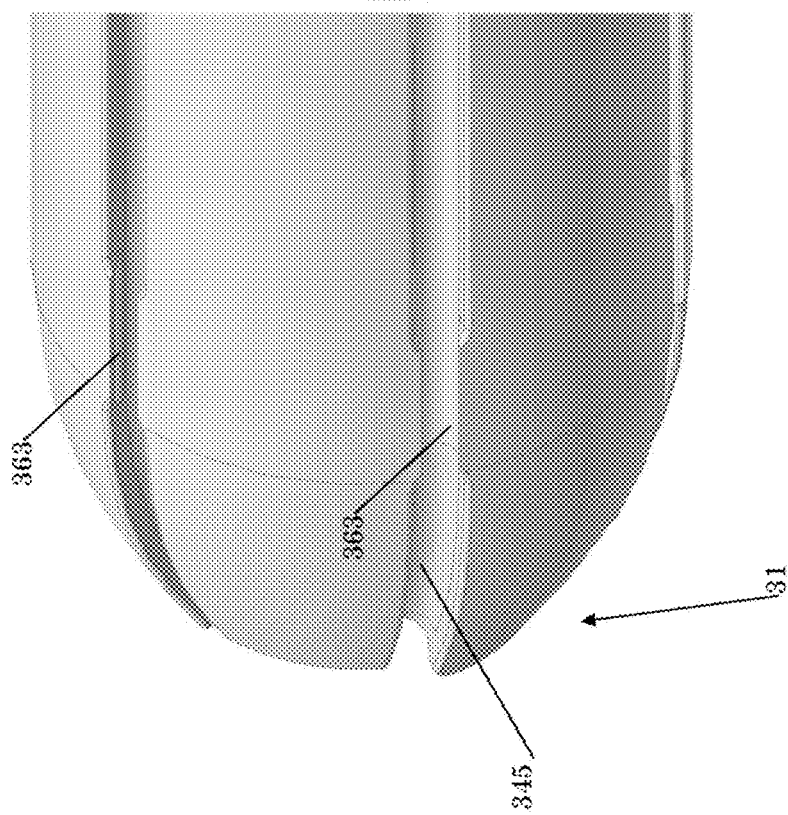
Figure 8A
Figure 8B

BRACHYTHERAPY APPLICATOR DEVICE FOR INSERTION IN A BODY CAVITY

This application is a division of U.S. application Ser. No. 13/807,552, filed on Apr. 8, 2013, which is a U.S. national stage filing under 35 U.S.C. § 371 of International Application No. PCT/NL2011/050474, filed on Jun. 30, 2011, which claims priority to Netherlands Application No. 2005005, filed on Jun. 30, 2010, and U.S. Provisional Application No. 61/365,004, filed on Jul. 16, 2010, all of which are incorporated herein by reference.

FIELD

The invention relates to a brachytherapy applicator device for insertion in a body cavity. In particular, the invention relates to a brachytherapy applicator device for irradiating tumours.

BACKGROUND

DE4413490 shows such an instrument of the cylindrical vaginal applicator type, where irradiation positions are realized by a central catheter which is introduced into the applicator. The applicator can be connected to a so-called remote afterloading machine which via tubes moves a radioactive source to an irradiation position in the central catheter. In this device some radiation shielding is provided by a central filler element which is inserted in the applicator and can be made from different materials to provide differential radiation shielding with a relatively limited control over the dose distribution.

Such an applicator may comprise multiple catheters provided along a wall part of the cylinder, which thereby generally follows the form of the body cavity wherein the applicator is inserted. The guidance of the catheters along the wall part enables the irradiation doses to be shaped and so optimised, whilst keeping the dose at the surface of the organ at or below the desired limit. The irradiation is done by bringing a radiation source provided at the end of a guide cable via a transfer tube and the catheter to a predetermined correct position and allowing it to deliver radiation there for a predetermined length of time to combat the tumour.

It is noted that conventional applicators are instruments assembled from complex parts and frequently comprise long guide through bores that are difficult to clean when sterilizing the instruments for repeated use.

It is an object of the invention to provide an instrument which can be assembled quickly and introduced easily into the body cavity and whose positioning is accurate and reliable. In addition, it is an object to provide an instrument that is easily dis-assembled and so can easily be cleaned and sterilized.

SUMMARY

According to an aspect, a brachytherapy applicator device is provided for insertion in a body cavity, comprising an applicator shaped for insertion in the body cavity; the applicator comprising connectable parts;

at least one connectable part having a form following wall surface shaped to follow the body cavity, the wall surface having a multichannel groove structure, so as to guide a plurality of catheters along the grooves in the groove structure along the wall surface.

The groove structure provides efficient and reliable guiding of irradiation catheters at a predetermined distance from the cavity wall while at the same time being easy to clean. In addition, the segments allow for quick assembly and disassembly of the applicator, so that the constituting segments are exposed for cleaning.

EXEMPLARY EMBODIMENTS

The invention will be elucidated in more detail in and by a description of the drawings, in which:

FIGS. 8a and 8b shows a detailed view of the distal and proximal parts respectively.

In the drawings, the same or corresponding parts are designated by the same reference numerals.

Figure 1:
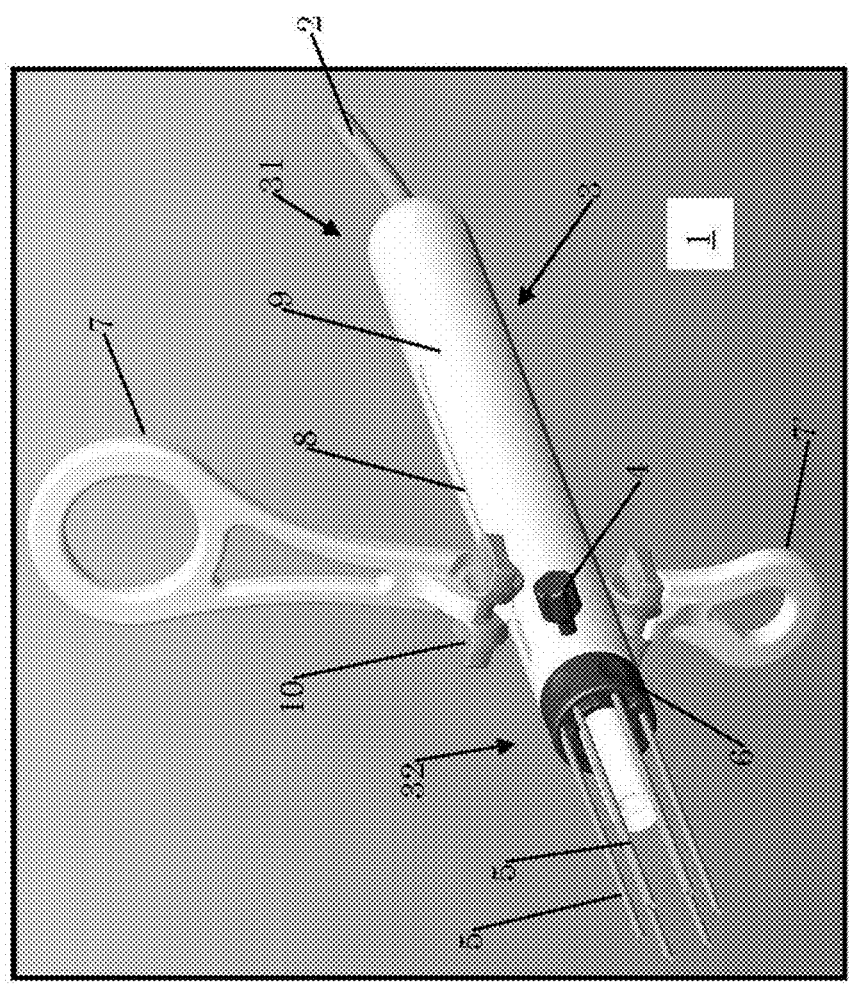
FIG. 1 shows a complete assembly of an applicator device.

FIG. 1 shows a complete assembly of an applicator device 1. In assembled condition, a brachytherapy applicator device 1 is provided for insertion in a body cavity. The assemblies and components described herein would be suitable for administration of all types of brachytherapy treatment. This applicator can be used for treatment of gynaecological tumours of the vagina and cervix and can also be used for the treatment of colo-rectal tumours or those affecting the endo-metrium. During brachytherapy treatment energy emitting (radioactive) sources are inserted near or into the tumourous tissue of the human or animal body to be treated. For this purpose, an active energy emitting source is used to administer what is generally known as High Dose Rate (HDR) treatment. In HDR treatment the radiation source is guided into the tissue or body cavity for one or more periods by means of a needle or a catheter and is always contained within a closed capsule so it never comes into direct contact with the tissue. Brachytherapy can also be performed with PDR (pulse dose rate) or LDR (low dose rate) treatments. In addition, as long as the applicator is shaped in a corresponding effective form the applicator device may be used for any intracavitary or interstitial treatment.

In this embodiment the version of the applicator, which comprises a plurality of connectable parts, could be used for treatment of gynecological tumours of the vagina and cervix will be described. In more detail, the embodiment shows further an optional central intrauterine tube 2 that can be fixed relative to the applicator 3 and which is guided through a central opening in the dome-shaped distal end 31 of the applicator 3. The intra-uterine tube 2 is provided with a positioning means 4 for fixation relative to the applicator.

This means comprises in the exemplary embodiment a fixation screw. In this embodiment, the intra-uterine tube is of fixed length, but an adjustable length tube could be used. In a further alternative, different angles can be used to provide suit different patient anatomies. The intra-uterine tube 2 accordingly serves for insertion into the cervix and can be used for intrauterine irradiation. Exemplary for an applicator form shaped for insertion into the body cavity, is a multi-channel cylindrical type of the present embodiment, which has a form following wall surface shaped to follow the body cavity. In this embodiment, the applicator comprises a plurality of guiding grooves in the wall for guiding catheters 5 along their respective longitudinal axes and restrain the catheters 5 against motion in a direction away from their longitudinal axes. In addition the device 1 further comprises a catheter locking structure, in this example in the form of a cap 6 on the proximal part 32 further detailed in FIG. 4 and FIG. 6 that locks the catheters 5 against axial movement relative to the applicator 3. After placement, during the irradiation, a high dose can be delivered to the base of the uterus without the surrounding organs such as large intestine and bladder needing to be irradiated unduly heavily. Preventing this excessive irradiation is of major importance since otherwise serious complications may be expected. A connectable handle 7 known as a perineal bar is slidingly engageable in a corresponding slot 8. The slot 8 is arranged along an outer surface 9 of the applicator 3. For fixation, a knob or lever 10 is provided which fixes the perineal bar 7 relative to the groove 8. The knob 10 has a cam structure which fixes the bar 7 when rotated. The perineal bar can be selectively provided in various sizes 7, 7' and fixed on one or either side of the applicator 3.

Figure 2:
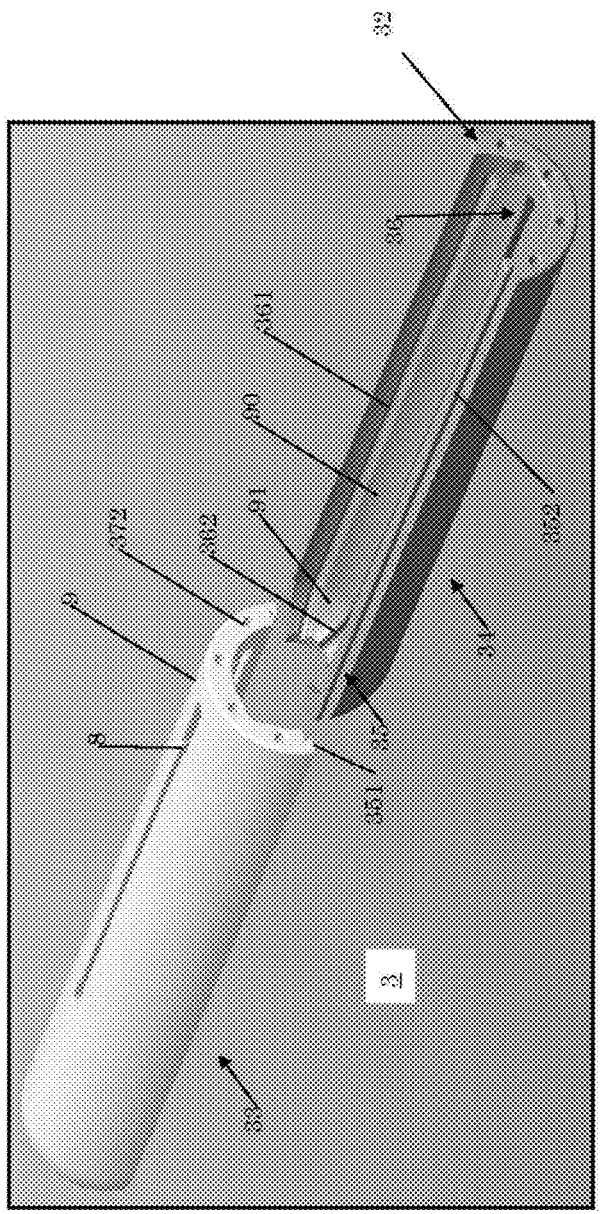
FIG. 2 shows a perspective view of a two-piece applicator of the applicator device in disassembled condition.

FIG. 2 shows the applicator 3 in more detail. The applicator is formed by two connectable parts 33 and 34 having connectors 35 for ready connection. The connectors 35 are provided by mating shoulder pieces or wedges 351, 352, each arranged on opposite end sides of the connectable segments 33, 34 each forming a partly tubular shaped segment. Alternatively a fastener 35 can be provided by, for example, in the forth of a locking groove and a locking knob to be locked in sliding engagement in a corresponding locking slot. An alternative locking structure may for example be provided by a dovetail type joint providing interlocking with conventional locking shapes.

The wall surface comprising the groove structure 36 is advantageously distanced from the body surface, but this is not essential; it may be formed as an outer surface that is in direct contact with the body cavity or by a surface distanced from the outer surface such as in the present example. In this example, inner wall surface 90 has a multichannel groove structure 36 that is provided to guide the catheters 5 along grooves 361 in the groove structure 36 along the wall surface. Alternatively, the groove structure 36 may be provided on the outer surface 9, in addition to the locking slot 8 for the perineal bar 7 (see FIG. 1).

Figure 2A:
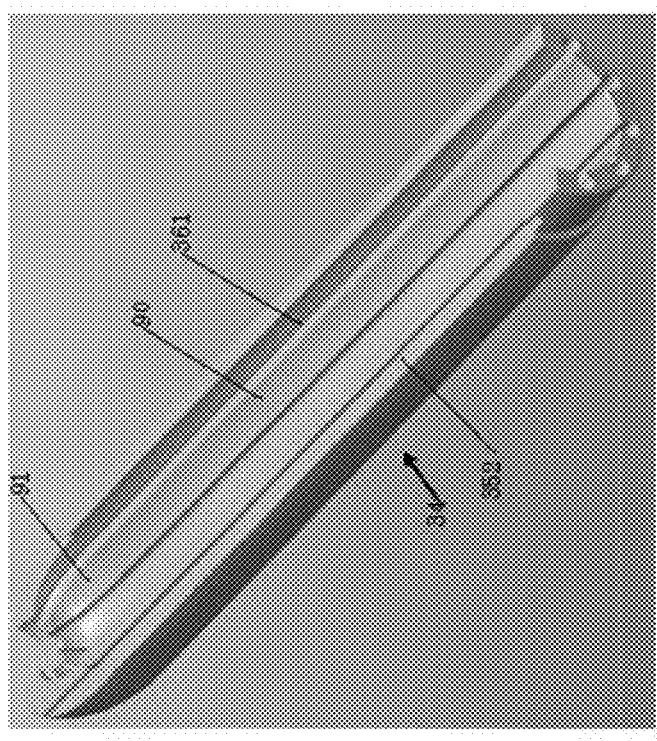
FIG. 2A shows a sectional view of an alternative segment of the applicator.

The grooves 361 may be formed as open trench structures that can be the continuations of through holes 372 of a relatively short depth that may be provided on the segment edges, in particular, the proximal part 32 thereof. Alternatively, the grooves may be continued without through holes 372, as shown in FIG. 2A. While FIG. 2 shows an applicator comprised of two segments 33, 34, the tubular applicator could be formed of more segments which may be connected together. Each segment may be provided with one or more grooves 361 on inner wall 90.

Figure 2B:
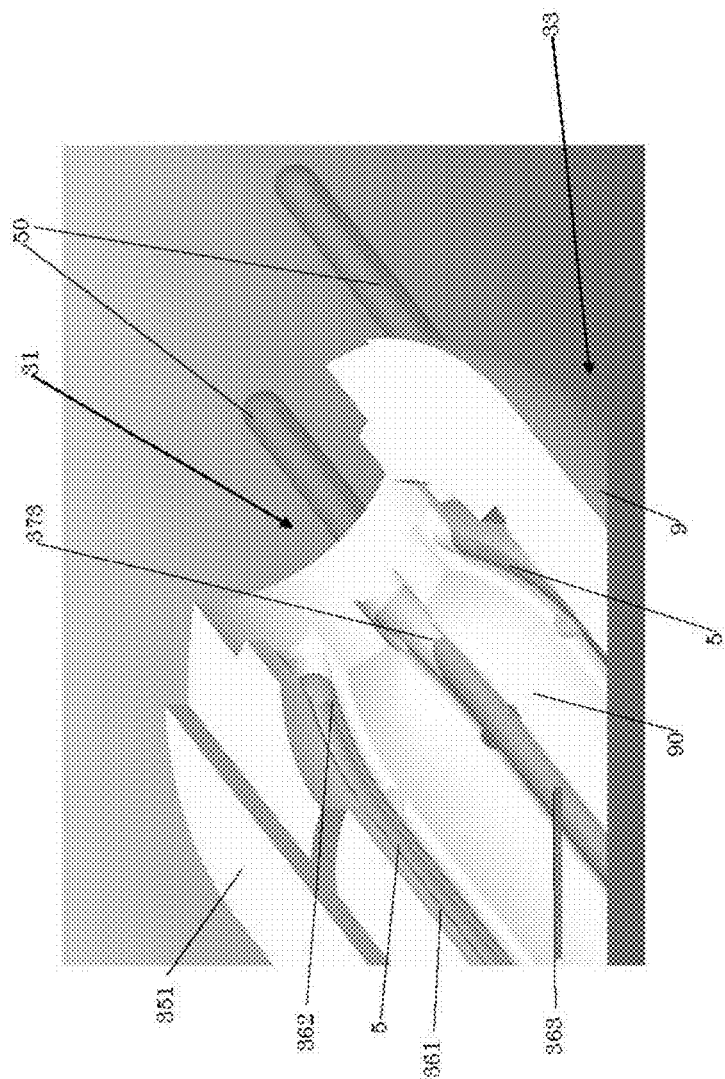
FIG. 2B shows a sectional view of a further alternative segment of the applicator.

In a further alternative, shown in FIG. 2B, in a sectional view of a segment 33, in particular, its dome shaped distal part 31, through hole guides 373 can be combined with open grooves 363 arranged on inner wall 90 to provide a (nearly) straight catheter guide for a catheter 50 extending from a groove 363 in axial direction out of the dome shape 31 via through holes 373. The concept here is that a further groove structure may comprise grooves 363 extending via respective through holes 373 out of the dome shape 31 so that a catheter 50 following the further groove structure continues straight on out of the applicator and is capable of penetrating the surrounding tissue.

The connecting functionality of the structure is similar in as the FIGS. 2 and 2a embodiment with a wedge 351 arranged for mating with a corresponding wedge of another segment (not shown).

Figure 2C:
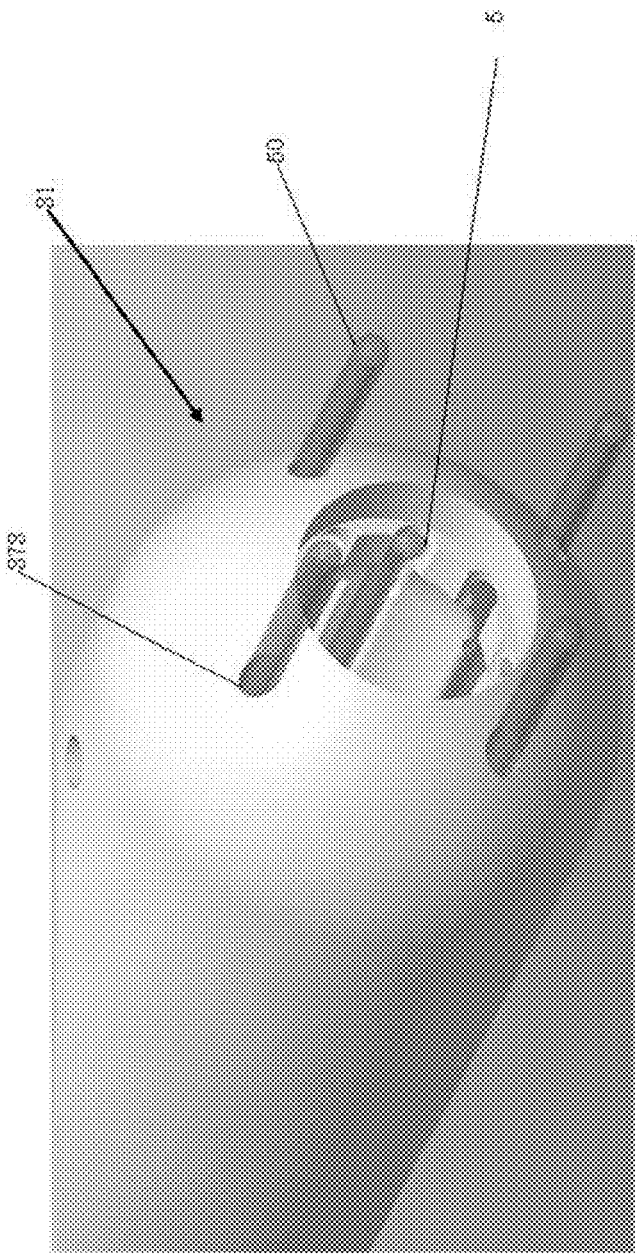
FIG. 2C shows a front perspective view of the alternative segment.

An important aspect of the grooves, in addition to their favourable cleaning properties, is that they facilitate in guiding the catheter along curved surface 91, particularly for instance, in the dome shaped distal end 31 where the segment 34 is shaped to have a rounded inner wall part 91 comprising a groove 362 curved in the axial direction along a center axis of the applicator. FIG. 2C shows a schematic front view of dome shape 31

Accordingly, in the embodiment of FIGS. 2B and 2C, a catheter 5 may follow the groove structure 36 radially around the dome shape 31 via curved groove 362; or a catheter 50 may follow a straight guiding path via a through hole 373. The catheters 5, 50 may be of the same kind, or may be formed purposely, for example, a straight catheter 50 may be more rigid than a curved catheter 5.

Advantageously, the grooves with a grooved path 361, grooves with a straight path 363 may at least partly lie on a same (semi) circular circumference of the tubular segment 33, 34, in particular, on its inner wall 90. Conversely, grooves may be arranged on the outer wall as illustrated in the example below, or in a mixed form with both walls, for example, straight grooves arranged on the outer wall and dome shaped grooves on the inner wall 90. In addition, for example, through hole guides can also be arranged near a wall part 9 opposite the groove structure on the inner wall 90, so that radiation can be provided via further catheters arranged in through hole guides axially following the outer wall 9 (not shown).

The curved grooves are important in improving the dose distribution at the distal end 31 of the applicator. With this curved guidance of the catheters, the cervix area can be reached better so helping to improve dose distribution with the aim of optimizing the radiation treatment.

Whilst the drawings in FIG. 2 show two semi-cylindrical segments which can be connected together this can be formed by more than two components, for example, three or four semi circular segments. Each of those separate segments could therefore have a different configuration of channels for the catheter. Thus, a segment could only comprise "straight-through" channels such as grooves 363 and another could be or include the curved grooves 361. An advantage of the multiple segments is that different types of segment could be selected and the applicator could almost be "customised" to provide a specific dose profile according to the need of the patient. Accordingly, multiple segments can each be provided with a designated groove structure.

Figure 3:
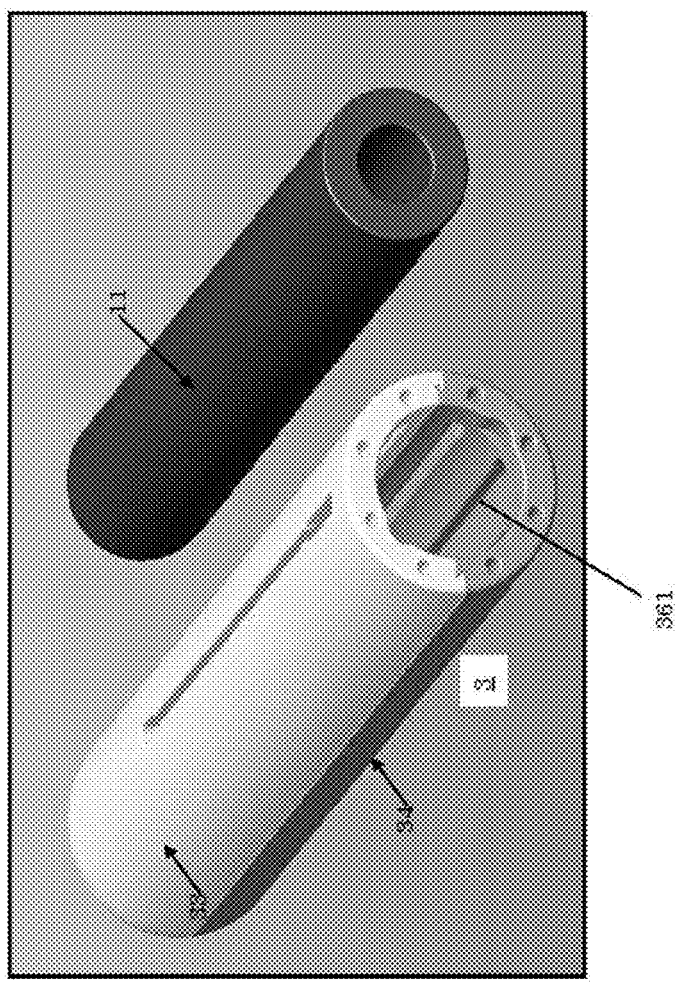
FIG. 3 shows a perspective view of the applicator of FIG. 2 in assembled condition.

FIG. 3 shows the segments 33 and 34 in assembled condition. A filler tube 11 may be provided. Advantageously the filler piece 11 may comprise a plurality of interlocking segments (not shown) made from different materials having different radiation shielding properties, which can differentially reduce the dose of the radiation emitted from the catheters and passing through the applicator. This is advantageous for calculation purposes. Optionally the filler tube could be formed from a plurality of interlocking segments arranged in such a manner to tune the radiation profile. The filler tube 11 may form a close fit inside the cylindrical segments 33 and 34 for ensuring the catheters remain inside the grooves 361. Alternatively, as shown in the present embodiment, the groove structure comprises a groove 361 that locks the catheter along a more than semicircular circumference.

The present embodiment thus forms a brachytherapy applicator device for insertion in a body cavity, comprising an applicator 3 shaped for insertion in the body cavity; the applicator 3 comprising a plurality of connectable parts 33, 34 at least one of the connectable parts 33, 34 having a first wall surface 9 shaped to follow the body cavity, a second wall surface 90 having a plurality of catheter guide grooves 36 therein capable of guiding a catheter 5 along a groove 361, a third wall surface 11 cooperating with the second wall surface 90 to maintain the catheter in the groove when the applicator is assembled.

Figure 4:
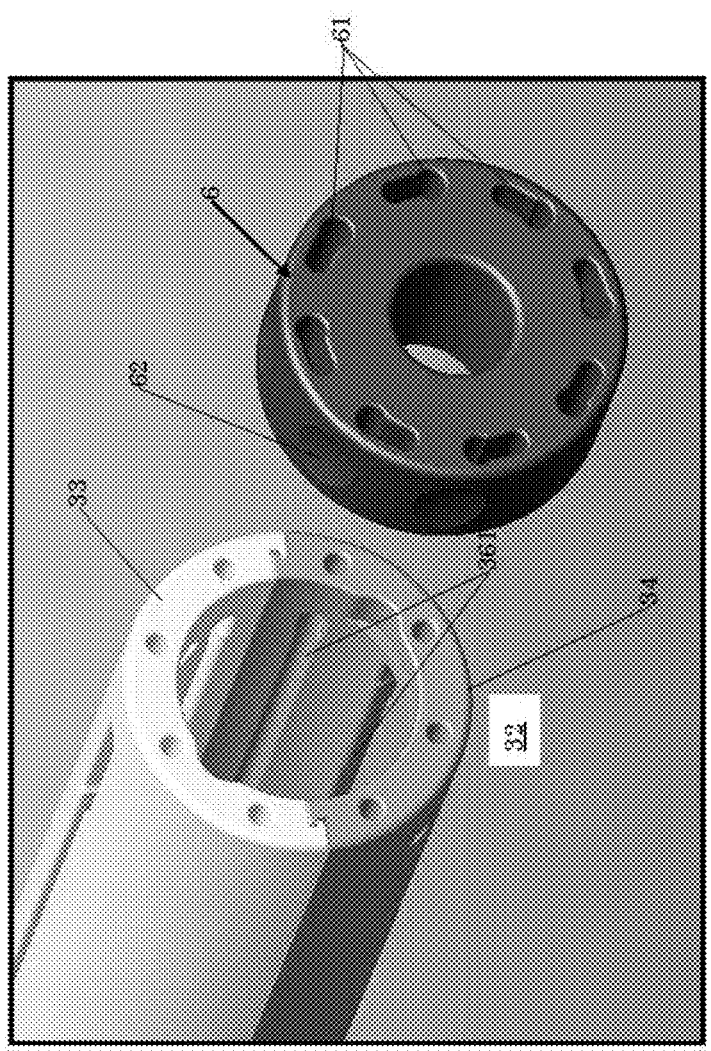
FIG. 4 shows a view of proximal part of the applicator of FIG. 3 in disassembled condition.

FIG. 4 shows in more detail the applicator's proximal end 32 and cap 6. The cap 6 may be optionally provided and has advantageous locking features. Not shown are connectors of cap 6 connectable to the cylinders' proximal end 32. For locking the catheters, the cap 6 comprises a catheter locking structure 61 aligned with the groove structure 361. In the example, the catheter locking structure 61 is formed by keyholes provided in the cap 6 and aligned with a corresponding groove 361 in the cylinder segments 33, 34. The cap 6 can be rotated to lock the catheter 5 in the keyhole 61. Accordingly, cap 6 is to guide catheters 5 through keyholes 61 and has a central opening for passing of the intrauterine tube 2. Depressions 62 are provided for providing grip.

Figure 5:
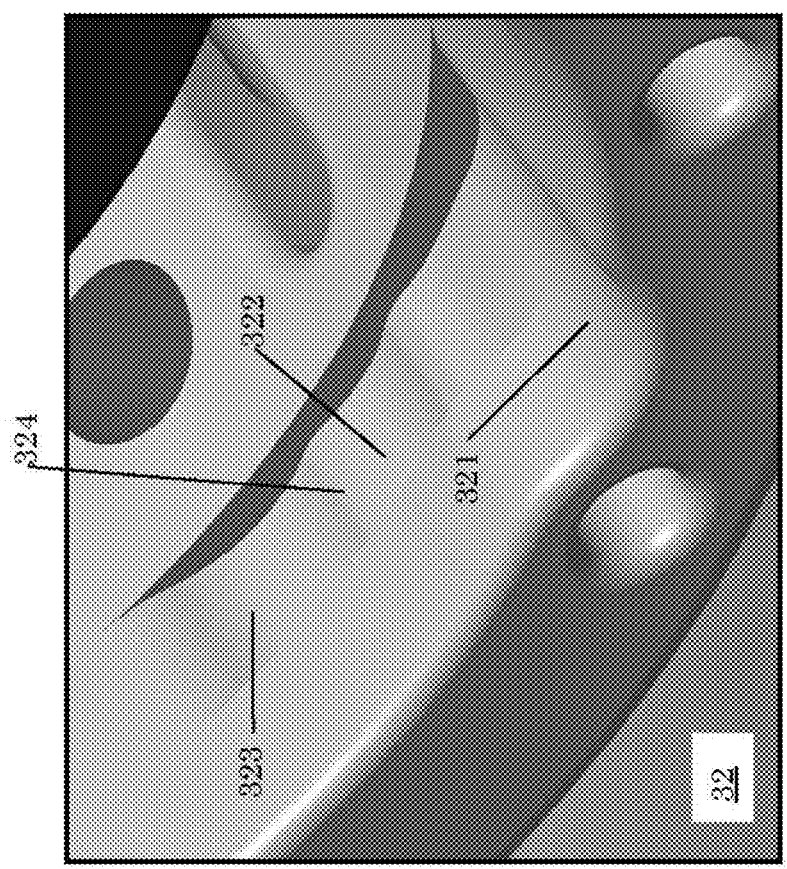
FIG. 5 shows a detailed view of the proximal part of FIG. 2.

As an example of a cap connector structure, FIG. 5 shows a detail of a proximal end 32 of the applicator, in particular, L-shaped recess 321. The cap connectors are formed by resilient locking knobs (not shown). The recess 321 accordingly receives a knob provided on cap 6 (not shown) and can be clicked in the recess 321 from an unlock to a lock position (322, 323) via a local thickening 324 provided in the recess 321.

Figure 6:
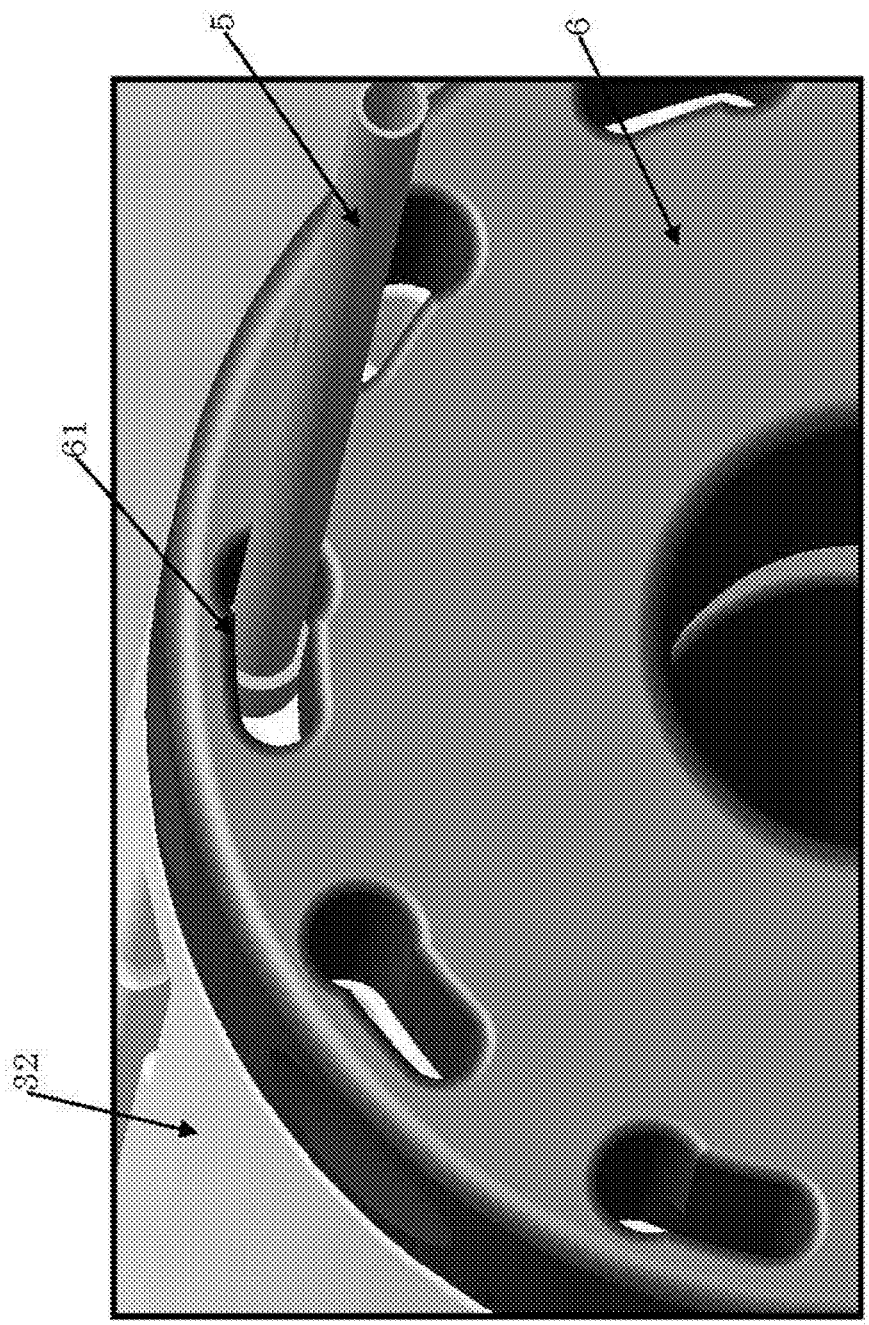
FIG. 6 shows a schematic perspective view of the keyhole structure in the proximal part in particular.

FIG. 6 shows the cap 6 in mounted position, wherein it can be seen that a catheter 5 is provided that is guided through keyhole 61 and is shown in locking position.

Figure 7:
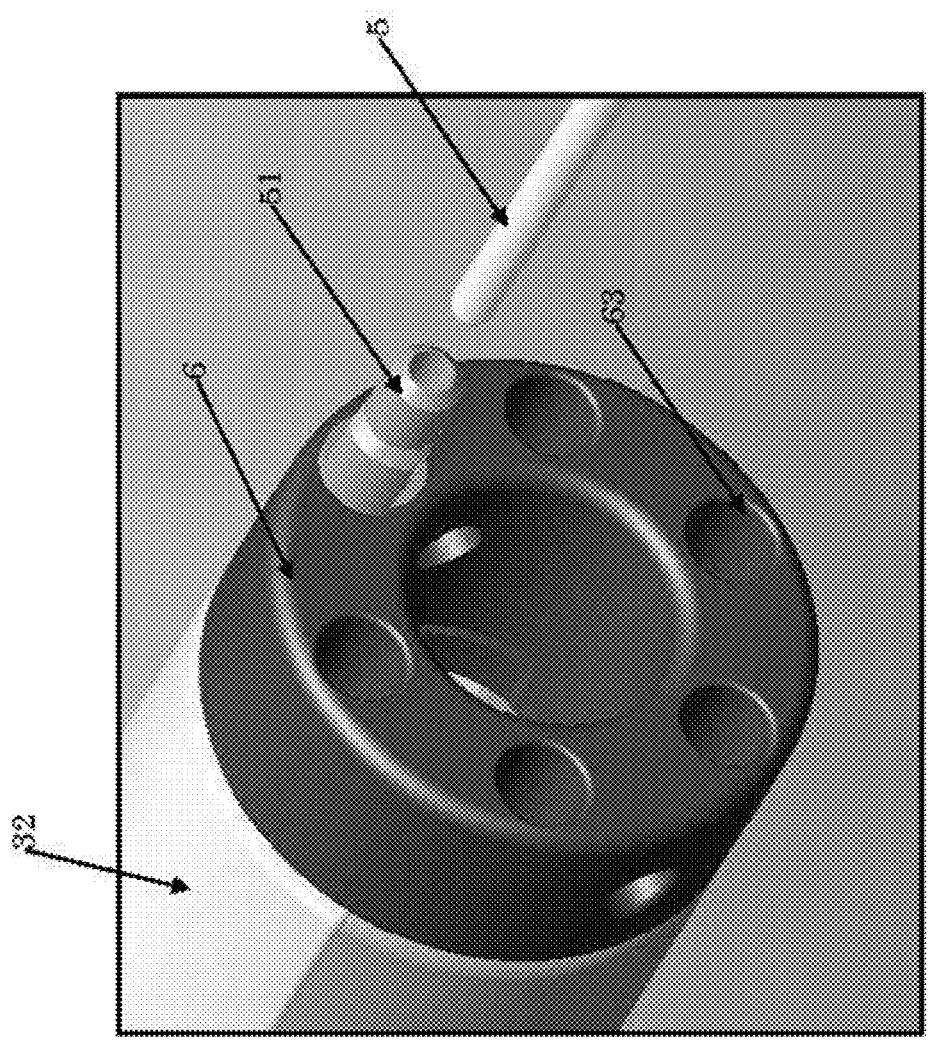
FIG. 7 shows an alternative cap structure.

FIG. 7 shows an alternative locking mechanism, wherein the locking structure is formed by catheter locking insert 51 to be inserted in a corresponding recess 63 arranged in the cap. By way of example, such inserts 51 can fixate the catheter 5 by twisting it in a corresponding threaded part or by a bayonet click conventionally known.

Figure 8:
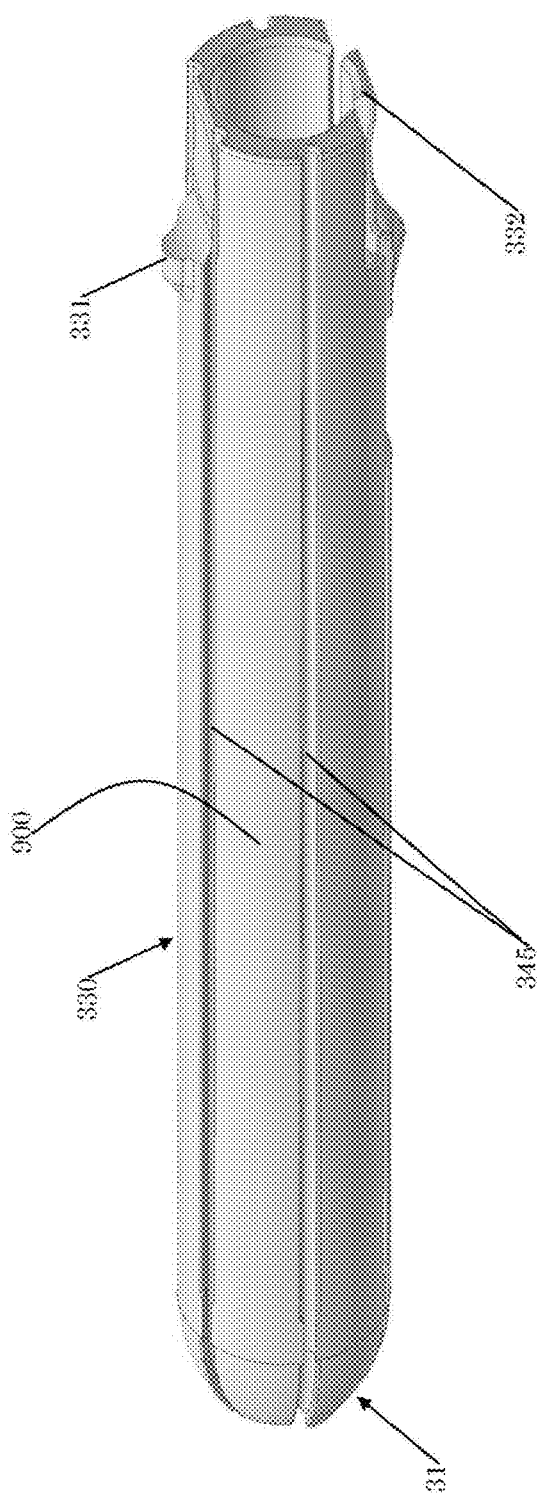
FIG. 8 shows a connectable part of an alternative applicator device

FIG. 8 shows a connectable part comprising a core piece 330 of an alternative applicator device. In this embodiments, the core piece 330 is not segmented but tubular shaped and forms a core piece of the applicator device 30 illustrated in more detail in the following figures. The core piece 330 has an elongated rounded form shaped for insertion into a cylinder 340 (see FIG. 9) which has a substantially smooth inner wall surface. The cylinder 340 forms an outer sleeve of an applicator device which can be inserted into a body cavity such as the vagina or rectum. The core piece 330 has a multichannel groove structure 36 on the outer surface of the wall 900, to guide a plurality of catheters along the grooves 345 in the groove structure along the outer wall surface 900.

FIG. 8a shows a detailed view of the distal part of the core piece 330, where it can be shown that the applicator has a dome-shaped distal end portion 31, the groove 345 extending into the distal dome shaped end portion and curved towards a central region of the dome 31. In addition, tongue structures 363 are used to enclose more than a semicircular circumference in order to retain the catheter (not shown) in the groove. In use, brachytherapy catheters can be easily inserted in and removed from the groove structure 345, prior to assembly or disassembly.

FIG. 8b shows a proximal view of the core piece 330. A cap 60 is connectable to a proximal end of the applicator core piece 330 via a slot 64 that engages a knob 331 on the core piece 330. The cap may include a catheter locking structure similar in operation as the previous embodiment which can lock or unlock by rotating the cap 60.

Figure 9:
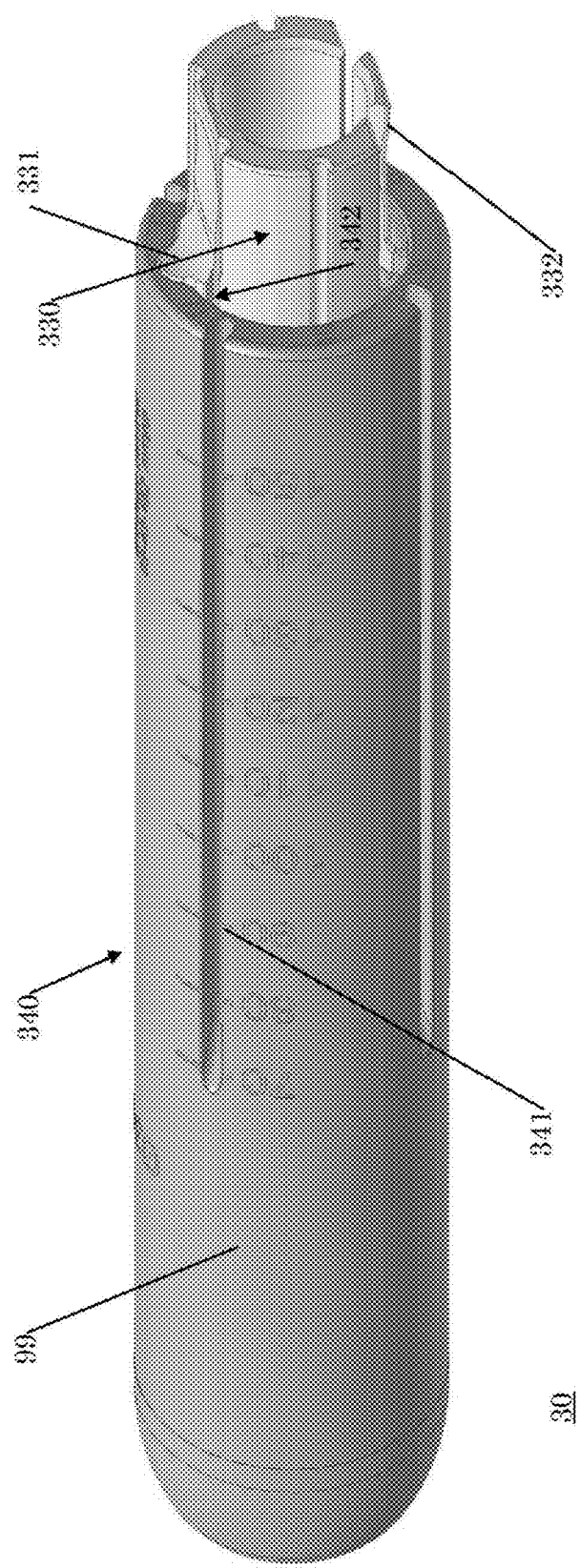
FIG. 9 shows the applicator device having a sleeve structure slided on the connectable part.

FIG. 9 shows the applicator device having a sleeve 340 connected over the core piece 330 in assembled form. The sleeve 340 is located in the correct orientation over the core piece 330 by knob 331 engaging a cooperating slot on the outer sleeve 340 and maintained in position by a latching tooth which engages in a cooperating latching recess in the outer sleeve 340. The pressbar 332 arranged on the core piece 330 can be pressed inwards towards the centre of the core piece to release the parts. The sleeve 340 discloses marks 341 for accurately locating a sliding a bar similar to the perineal bar 7 disclosed in FIG. 1. Alternatively, the marks can be used as an indication of the depth of insertion of the applicator into the body cavity.

The present embodiment thus forms a brachytherapy applicator device for insertion in a body cavity, comprising an applicator 30 shaped for insertion in the body cavity; the applicator 30 comprising a plurality of connectable parts 330, 340 at least one of the connectable parts 330, 340 having a first wall surface 99 shaped to follow the body cavity, a second wall surface 900 having a plurality of catheter guide grooves 345 therein capable of guiding a catheter 5 along a groove 361, a third wall surface 342 cooperating with the second wall surface 900 to maintain the catheter in the groove 345 when the applicator is assembled.

The insert piece and catheters are preferably made from a plastics material. Preferably, the catheters are sufficiently flexible to allow bending in the groove structure. Although the invention has been elucidated with reference to the examples shown in the drawings, the invention is not limited thereto but may also comprise variations or modifications without deviating from the spirit of the invention. The groove structure may be formed in an applicator outer surface directly in contact with the body cavity. In addition, where the text refers to a tubular shape, these shapes are understood to encompass any suitable round or elliptical forms and which may be of cylindrical, sleeve form and even slightly curved along the length axis. The scope of the invention is determined by the following claims.

The invention claimed is:

1. A brachytherapy applicator device for insertion in a body cavity, comprising:
    a tubular applicator shaped for insertion in the body cavity and comprising a tubular wall and a dome-shaped distal end, wherein the tubular wall comprises at least two segments connectable to each other along a length of the tubular wall, each shaped to define a partly tubular portion of a circumference of the tubular wall, wherein the at least two segments, when connected, form the circumference of the tubular wall and enclose a central opening extending along the length of the tubular wall;
    wherein at least one of the connectable segments has a form following wall surface shaped to follow the body cavity, and wherein an inner wall surface of the at least one of the connectable segments has a multichannel open groove structure contained in the central opening by the tubular wall and distanced from the form following wall surface, so as to guide a plurality of catheters along grooves in the groove structure along the inner wall surface of the at least one of the connectable segments, wherein the plurality of catheters inserted into the tubular applicator will follow the groove structure radially around the dome-shaped distal end.

2. The brachytherapy applicator device according to claim 1, wherein the tubular applicator comprises a filler piece.

3. The brachytherapy applicator device according to claim 2, wherein the filler piece retains a catheter of the plurality of catheters in the groove structure.

4. The brachytherapy applicator device according to claim 2, wherein the filler piece comprises a plurality of interlocking segments, each configured to interlock with a corresponding one of the plurality of interlocking segments, the interlocking segments made from one or more materials having different radiation shielding properties.

5. The brachytherapy applicator device according to claim 1, wherein each of the connectable segments comprises mating surfaces arranged on opposite end sides of the connectable segment, each mating surface being configured to mate with a corresponding mating surface of an adjacent connectable segment.

6. The brachytherapy applicator device according to claim 1, further comprising a central intrauterine tube configured to be fixed relative to the tubular applicator and which extends from a central opening in the dome-shaped distal end.

7. The brachytherapy applicator device according to claim 6, wherein the tubular applicator comprises a filler piece and wherein the central intrauterine tube is fixed relative to the filler piece.

8. The brachytherapy applicator device of claim 1, wherein a first one of the connectable segments includes a first wedge, a second one of the connectable segments includes a second wedge, and the first wedge is configured to mate with the second wedge to join the first and second connectable segments.

9. The brachytherapy applicator device of claim 1, wherein a first one of the connectable segments includes a locking groove and locking knob, a second one of the connectable segments includes a corresponding locking slot, and wherein the locking groove and locking knob are configured to be in sliding engagement with the locking slot to lock the first and second connectable segments together.

10. The brachytherapy applicator device of claim 1, wherein the at least two connectable segments comprises more than two segments.

11. A brachytherapy applicator device for insertion in a body cavity, comprising:
a tubular applicator comprising a tubular wall and a dome-shaped distal end, wherein the tubular wall comprises:
a first connectable segment semi-tubular shaped and forming a portion of a circumference of the tubular wall; and
a second connectable segment semi-tubular shaped and forming a second portion of the circumference of the tubular wall, the first portion and the second portion forming the circumference of the tubular wall and enclosing a central opening extending along a length of the tubular wall,
wherein the first connectable segment is coupled to the second connectable segment along the length of the tubular wall extending between first and second ends of the tubular wall, and wherein an inner wall surface of at least one of the first connectable segment and the second connectable segment has a multichannel groove structure configured to guide a plurality of catheters inserted into the tubular applicator to follow the groove structure radially around the dome-shaped distal end.

12. The brachytherapy applicator device of claim 11, wherein the first connectable segment comprises the inner wall surface having a plurality of straight grooves formed therein and configured to receive the plurality of catheters.

13. The brachytherapy applicator device of claim 12, wherein the second connectable segment comprises a second inner wall surface having a plurality of curved grooves formed therein and configured to receive the plurality of catheters.

14. The brachytherapy applicator device of claim 12, wherein each of the plurality of straight grooves comprises an open groove.

15. The brachytherapy applicator device of claim 14, further comprising a filler piece segment adjacent the first inner wall surface of the first connectable segment and configured to secure the plurality of catheters in the plurality of open grooves.

16. A brachytherapy applicator device for insertion in a body cavity, comprising:
a tubular applicator comprising a tubular wall and a dome-shaped distal end, wherein the tubular wall comprises:
at least two connectable segments, each of the at least two connectable segments being semi-tubular shaped to form a portion of a circumference of the tubular wall, wherein the at least two connectable segments, when connected, form the circumference of the tubular wall and enclose a central opening extending along the length of the tubular wall, and wherein:
a first of the at least two connectable segments includes a first plurality of grooves contained in the central opening by the tubular wall and extending through a first inner wall of the first connectable segment, and
a second of the at least two connectable segments includes a second plurality of grooves extending through a second inner wall of the second connectable segment, the first plurality of grooves being provided in a different configuration than the second plurality of grooves, wherein a plurality of catheters inserted into the tubular applicator will follow the first plurality of grooves and the second plurality of grooves radially around the dome-shaped distal end.

17. The brachytherapy applicator device of claim 16, wherein the first plurality of grooves are provided in a straight groove configuration, and the second plurality of grooves are provided in a curved groove configuration.

18. The brachytherapy applicator device of claim 16, wherein the first connectable segment is coupled to the second connectable segment along a length of the tubular wall extending between first and second ends of the tubular wall.

19. The brachytherapy applicator device of claim 16, wherein the at least two connectable segments comprise more than two segments.

* * * * *